US00PP09783P

United States Patent [19]

Zaiger et al.

[11] Patent Number: Plant 9,783

[45] Date of Patent: Jan. 21, 1997

[54] CHERRY TREE 'EARLISWEET'

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 550,600

[22] Filed: Oct. 31, 1995

[51] Int. Cl.[6] ..... A01H 5/00

[52] U.S. Cl. ..... Plt./37

[58] Field of Search ..... Plt./37

[56] References Cited

PUBLICATIONS

Topp, et al., (1990) "'Queensland Earlisweet' Cherry Plum", *HortScience* 25(6):713.

*Primary Examiner*—James R. Feyrer

[57] ABSTRACT

A new and distinct variety of cherry tree, *Prunus avium*, which has the following unique combination of features that are desirable in a new variety:

1. Early maturity of fruit.
2. Fruit with good flavor and eating quality.
3. Heavy and regular production of medium size fruit.
4. Vigorous, upright growth.
5. Fruit with an attractive red skin color.

1 Drawing Sheet

ORIGIN OF THE VARIETY

The present new variety of cherry tree was originated by us in our experimental orchard located near Modesto, Calif., from a selected seedling from an open pollinated Stella Cherry (non-patented) seed. A large group of the open pollinated seedlings were grown and maintained under close observation, one such early maturing seedling, which is the present variety, having especially desirable fruit characteristics was selected for asexual reproduction and commercialization.

ASEXUAL REPRODUCTION OF THE VARIETY

Asexual reproduction of the new and distinct variety of cherry tree was done by budding, as performed by us in our experimental orchard located near Modesto, Calif. and shows that all characteristics of the tree and its fruit run true to the original tree and are established and transmitted through succeeding asexual propagations.

SUMMARY OF THE VARIETY

The present new and distinct cherry tree is of large size, vigorous and upright growth, and is a regular and productive bearer of early maturing, medium size fruit with good flavor and eating quality. The fruit is further characterized by being relatively uniform in maturity, having good handling and shipping quality, having a high degree of attractive red skin color, and ripening approximately 23 days before the Stella Cherry (non-patented).

PHOTOGRAPH OF THE VARIETY

The accompanying color photographic illustration shows typical specimens of the foliage and fruit of our new cherry variety. The illustration shows the upper and lower surface of the leaves, an exterior and sectional view of the fruit divided in the suture plane to reveal flesh coloration, pit cavity and a stone remaining in place. The photograph was taken shortly after the fruit was picked at maturity (firm ripe), and the colors are as nearly true as is reasonably possible in a color representation of this type.

DESCRIPTION OF THE VARIETY

The following is a detailed botanical description of the new variety of cherry tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Bearing.*—Regular.
- *Productivity.*—Productive.

Trunk:
- *Size.*—Large.
- *Texture.*—Medium stocky.
- *Color.*—Light brown to brown (7-D-3) to (7-E-4).

Branches:
- *Size.*—Medium.
- *Texture.*—Smooth to medium rough, varies with age of growth.
- *Lenticels.*—Medium number. Large size.
- *Color.*—Golden brown to light brown, varies with maturity.

Leaves:
- *Size.*—Large. Average length 6". Average width 2".
- *Margin.*—Serrate.
- *Form.*—Obovate. Pointed.
- *Thickness.*—Medium.
- *Texture.*—Smooth.
- *Glands.*—Reniform. Size — medium. Number varies from 1 to 4. Average number 2. Primarily on upper portion of the petiole.
- *Petiole.*—Average length 2¼". Medium thickness.
- *Color.*—Upper surface — green to dark green (28-F-4) to 28-F-7). Lower surface — dull green to grayish green (28-E-4) to (28-E-5).

Flower buds:
- *Size.*—Large.
- *Length.*—Medium.
- *Form.*—Plump.

Flower:

*Size.*—Large.

*Blooming period.*—Date of first bloom — Mar. 14, 1994. Date of full bloom — Mar. 20, 1994.

*Color.*—White.

*Pollen.*—Present.

Fruit:

*Maturity when described.*—Moderately firm ripe.

*Date of first picking.*—May 4, 1994.

*Date of last picking.*—May 7, 1994.

*Size.*—Medium. Comparatively uniform. Average diameter axially ¾". Average transversely in suture 15/16".

*Form.*—Relatively uniform, Globose to slightly oblate.

*Suture.*—Shallow, relatively smooth.

*Ventral surface.*—Nearly rounded.

*Cavity.*—Circular. Average depth ⅛". Average width ¼".

*Base.*—Retuse.

*Apex.*—Rounded to slight depression.

Stem of fruit:

*Size.*—Average length 1⅛". Medium thickness.

Flesh:

*Texture.*—Moderately firm.

*Ripens.*—Evenly.

*Flavor.*—Mild, sweet, good balance between sugar and acid.

*Eating quality.*—Good.

*Juice.*—Moderate.

*Color of flesh.*—Light pink to red (10-B-5) to (10-B-7), varies with fruit maturity.

Skin:

*Thickness.*—Medium.

*Texture.*—Medium.

*Down.*—Wanting.

*Tendency to crack.*—None during dry weather. Slight during wet weather, varies with stage of fruit maturity.

*Color.*—Light red to red (10-B-8) to (10-C-8).

Stone:

*Type.*—Clingstone.

*Size.*—Average length 7/16". Average breadth ⅜". Average thickness ¼".

*Form.*—Oblong.

*Tendency to split.*—None.

*Apex.*—Rounded to slight apical point.

*Base.*—Round.

*Color.*—Light tan to tan (5-C-5) to (5-D-5).

Use: Dessert.

*Market.*—Local and long distance.

Keeping quality: Good.

Shipping quality: Good.

The present new variety of cherry tree, its flowers, foliage and fruit herein described may vary in slight detail due to climate, soil conditions, and cultural practices under which the variety may be grown; the present description is that of the variety grown under the ecological conditions prevailing near Modesto, Calif.

We claim:

1. A new and distinct variety of cherry tree, substantially as illustrated and described, characterized by its large size; vigorous, upright growth and being a regular and productive bearer of medium size, early maturing fruit with an attractive red skin color; the fruit is further characterized by being relatively uniform in ripening, having good flavor and eating quality, and ripening approximately 23 days before its parent Stella Cherry (non-patented).

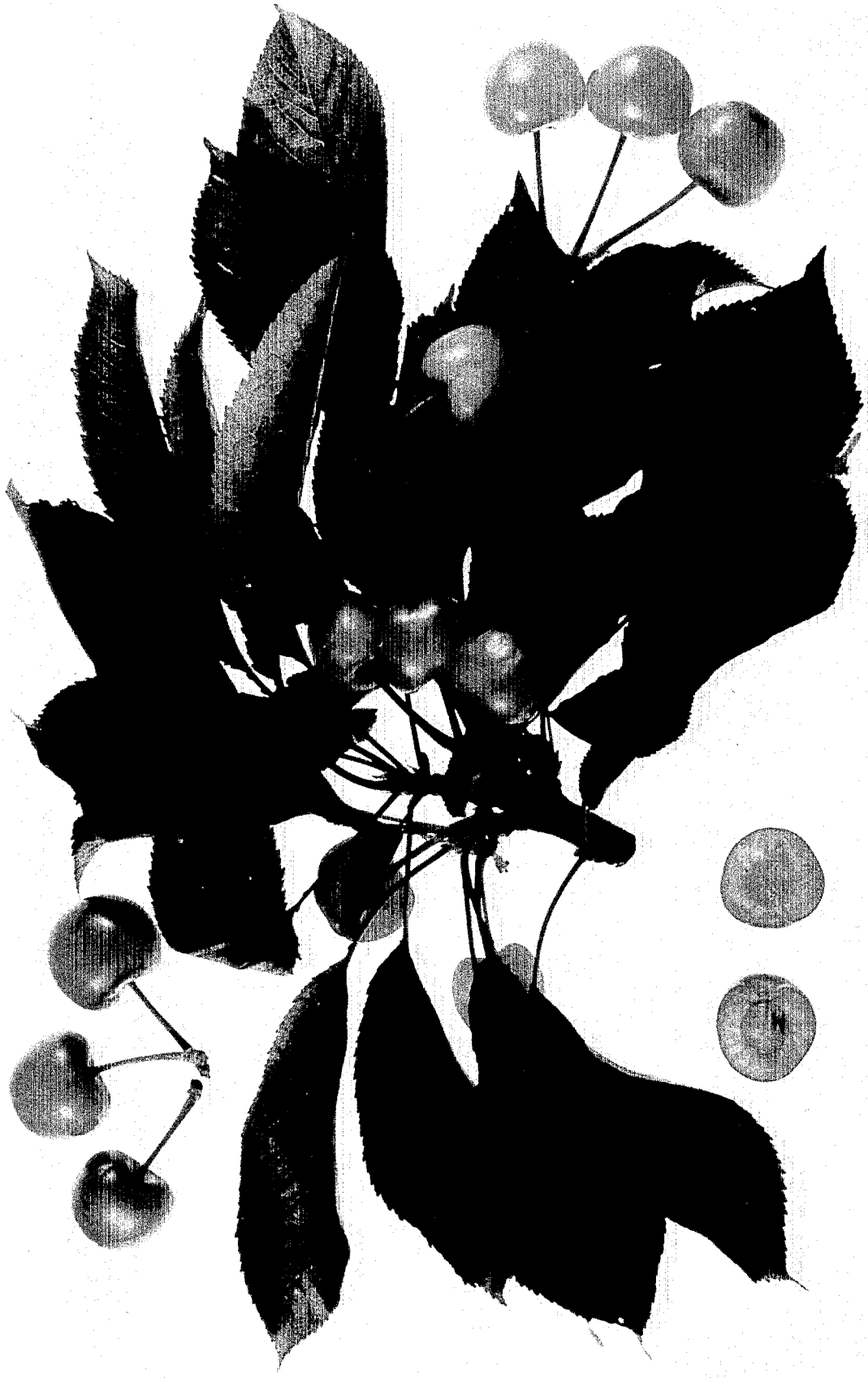

* * * * *